US010600615B2

(12) United States Patent
Xu et al.

(10) Patent No.: US 10,600,615 B2
(45) Date of Patent: Mar. 24, 2020

(54) ENHANCED FIB-SEM SYSTEMS FOR LARGE-VOLUME 3D IMAGING

(71) Applicant: Howard Hughes Medical Institute, Ashburn, VA (US)

(72) Inventors: C. Shan Xu, Ashburn, VA (US); Kenneth J. Hayworth, Ashburn, VA (US); Harald F. Hess, Ashburn, VA (US)

(73) Assignee: Howard Hughes Medical Institute, Ashburn, VA (US)

( * ) Notice: Subject to any disclaimer, the term of this patent is extended or adjusted under 35 U.S.C. 154(b) by 0 days.

(21) Appl. No.: 15/883,025

(22) Filed: Jan. 29, 2018

(65) Prior Publication Data

US 2018/0218878 A1 Aug. 2, 2018

Related U.S. Application Data

(60) Provisional application No. 62/451,460, filed on Jan. 27, 2017, provisional application No. 62/483,092, filed on Apr. 7, 2017.

(51) Int. Cl.
*H01J 37/28* (2006.01)
*H01J 37/31* (2006.01)
(Continued)

(52) U.S. Cl.
CPC .......... *H01J 37/28* (2013.01); *G01N 23/2251* (2013.01); *H01J 37/023* (2013.01);
(Continued)

(58) Field of Classification Search
CPC ......... H01J 2237/31745; H01J 37/3056; H01J 2237/31749; H01J 37/09;
(Continued)

(56) References Cited

U.S. PATENT DOCUMENTS 3,102,194 A * 8/1963 Van Den Broek et al. ................. H01J 37/224 250/311
5,136,171 A * 8/1992 Leung ................... H01J 37/026 250/251

(Continued)

FOREIGN PATENT DOCUMENTS

JP    H05314941 A    11/1993
JP    2015185457 A   10/2015

OTHER PUBLICATIONS

International Search Report and Written Opinion for PCT Application No. PCT/US2018/015798, dated Jul. 26, 2018, 23 pages.

*Primary Examiner* — David A Vanore
(74) *Attorney, Agent, or Firm* — Brake Hughes Bellermann LLP

(57) ABSTRACT

A microscopy system for imaging a sample can include a scanning electron microscope system configured for imaging a surface layer of the sample and a focused ion beam system configured for generating an ion beam for milling the surface layer away from a sample after it has been imaged. A movable mechanical shutter can be configured to be moved automatically into a position between the sample and the scanning electron microscope system, so that when the electron beam is not imaging the sample the movable mechanical shutter is positioned between the sample and the scanning electron microscope system.

15 Claims, 6 Drawing Sheets

(51) Int. Cl.
*H01J 37/30* (2006.01)
*G01N 23/2251* (2018.01)
*H01J 37/244* (2006.01)
*H01J 37/02* (2006.01)

(52) U.S. Cl.
CPC ........ *H01J 37/244* (2013.01); *H01J 37/3005* (2013.01); *H01J 37/3007* (2013.01); *H01J 37/31* (2013.01); *H01J 2237/022* (2013.01); *H01J 2237/024* (2013.01); *H01J 2237/0262* (2013.01); *H01J 2237/2067* (2013.01); *H01J 2237/3151* (2013.01); *H01J 2237/31745* (2013.01)

(58) Field of Classification Search
CPC ....... H01J 2237/0435; H01J 2237/2802; H01J 2237/30466; H01J 37/26; H01J 37/28; H01J 2237/026; H01J 2237/0455; H01J 2237/0458; H01J 2237/0807; H01J 2237/0815; H01J 2237/0817; H01J 2237/0835; H01J 2237/1514; H01J 2237/206; H01J 2237/2067; H01J 2237/2482; H01J 2237/30438; H01J 2237/3045; H01J 2237/30477; H01J 2237/3174; H01J 2237/31774; H01J 2237/31794; H01J 27/10; H01J 37/026; H01J 37/045; H01J 37/08; H01J 37/10; H01J 37/224; H01J 37/228; H01J 37/3005; H01J 37/3026; H01J 37/3171; H01J 37/3174; H01J 37/3177; G01N 1/32; G01N 23/225; G01N 1/04; G01N 1/06; B82Y 10/00; B82Y 40/00; G21K 5/04

USPC ..... 250/492.3, 492.21, 310, 311, 309, 492.2, 250/251, 306, 307, 396 R, 398, 491.1, 250/492.1, 492.22, 493.1, 494.1
See application file for complete search history.

(56) References Cited

U.S. PATENT DOCUMENTS

| | | | | |
|---|---|---|---|---|
| 5,525,806 | A * | 6/1996 | Iwasaki | G01N 1/32 250/310 |
| 5,986,264 | A | 11/1999 | Gruenewald | |
| 6,157,039 | A * | 12/2000 | Mankos | B82Y 10/00 250/492.2 |
| 7,928,377 | B2 * | 4/2011 | Ishitani | H01J 37/26 250/306 |
| 8,274,063 | B2 * | 9/2012 | Kaito | H01J 37/08 250/492.1 |
| 8,642,958 | B2 | 2/2014 | Takahashi et al. | |
| 2004/0031936 | A1 | 2/2004 | Oi et al. | |
| 2005/0184251 | A1 * | 8/2005 | Oi | H01J 37/28 250/492.3 |
| 2006/0065854 | A1 * | 3/2006 | Shichi | H01J 27/10 250/492.21 |
| 2006/0091321 | A1 * | 5/2006 | Kaga | G01N 23/225 250/491.1 |
| 2007/0158560 | A1 * | 7/2007 | Kaneoka | H01J 37/09 250/309 |
| 2008/0029699 | A1 * | 2/2008 | Kaneoka | G01N 23/225 250/307 |
| 2009/0220256 | A1 * | 9/2009 | Suhara | G03G 15/5037 399/32 |
| 2013/0164684 | A1 * | 6/2013 | Yamanaka | H01J 37/09 430/296 |
| 2016/0013012 | A1 * | 1/2016 | Sasaki | H01J 37/045 250/492.3 |

* cited by examiner

ENHANCED FIB-SEM SYSTEMS FOR LARGE-VOLUME 3D IMAGING

CROSS-REFERENCE TO RELATED APPLICATIONS

This application is a non-provisional of, and claims priority under 35 U.S.C § 119 to, U.S. Provisional Patent Application No. 62/451,460, filed Jan. 27, 2017, entitled "Enhanced FIB-SEM Systems for Large-Volume 3D Imaging," and to U.S. Provisional Patent Application No. 62/483,092, filed Apr. 7, 2017, entitled "Enhanced FIB-SEM Systems for Large-Volume 3D Imaging," the disclosures of both of which are incorporated herein in its their entireties.

BACKGROUND

Many modalities of electron microscopy (EM) can probe cellular structure at the nanometer scale. However, despite considerable progress over the past decade in developing high-resolution three-dimensional (3D) imaging, there remain important limitations reflecting an inherent trade-off between resolution and the size of the 3D volume. For demanding applications such as tracing neuronal processes, high resolution in the z axis, parallel to the direction of the electron beam of the electron microscope, in addition to the xy plane, is critical. Focused Ion Beam Scanning Electron Microscopy (FIB-SEM) offers this capability, with xy and z resolution all <10 nm. FIB-SEM can generate 3D images with superior z-axis resolution, yielding data with isotropic voxels that is therefore more readily interpretable than available with other techniques.

However, previous FIB-SEM approaches have been severely limited in the volumes that they could image, with typical volumes being less than the extent of a single neuron. For example, obstacles blocking wider adoption of FIB-SEM include slow imaging speed and lack of long-term system stability, which caps the maximum possible acquisition volume, dictated by the limited imaging speed and the limited duration of smooth and consistent ablation. Because the FIB process is destructive, there is little room for error in the ablation-imaging cycle, which requires virtually perfect continuity and consistency.

Thus, what is desired are techniques that accelerate image acquisition while also improving FIB-SEM reliability, allowing a FIB-SEM system to operate continuously for long time periods while generating large imaged volumes.

SUMMARY

In a general aspect, a microscopy system for imaging a sample can include a scanning electron microscope system configured for imaging a surface layer of the sample and a focused ion beam system configured for generating an ion beam for milling the surface layer away from a sample after it has been imaged. A movable mechanical shutter can be configured to be moved automatically into a position between the sample and the scanning electron microscope system, so that when the electron beam is not imaging the sample the movable mechanical shutter is positioned between the sample and the scanning electron microscope system.

Implementations can include one or more of the following features, alone or in combination with each other. For example, the movable mechanical shutter can includes a conductive element that is configured to monitor a current on the element. An electron beam produced by the scanning electron microscope system and the ion beam produced by the focused ion beam system can be oriented approximately perpendicular to each other. A normal direction to an imaged surface of the sample can be substantially parallel to a beam axis of electron beam produced by the scanning electron microscope system. The scanning electron microscope system can include a below-the-lens detector.

In another general aspect, a microscopy system for imaging a sample can include a focused ion beam system configured to direct a focused ion beam onto a sample, a scanning electron microscope system configured to direct an electron beam onto the sample, a plurality of charged-particle detectors, each detector being configured to monitor an electrical current on the detector, and a first controller configured to receive a plurality of signals indicative of the electrical currents on the plurality of charged particle detectors and configured to control automatically properties of a focused ion beam produced by the focused ion beam system in response to the received signals.

Implementations can include one or more of the following features, alone or in combination with each other. For example, the first controller can be configured to automatically prevent a focused ion beam produced by the focused ion beam system from striking the sample in response to at least one of the signals of the plurality of signals having a value that is outside a range of predetermined values. The first controller can be configured to automatically control the focused ion beam milling rate in response to at least one of the signals from the plurality of charged particle detectors. The plurality of charged particle detectors can include an inner Faraday cup configured to capture non-scattered ions produced by the focused ion beam system, and an annular Faraday cup configured to capture ions produced by the focused ion beam system and scattered by the sample. The plurality of charged particle detectors can include the sample. The sample can be maintained at a positive voltage bias, and the positive voltage bias can be selected to reject electrons below an energy threshold from entering the scanning electron microscope system. The plurality of charged particle detectors can include a movable shutter located between the sample and the scanning electron microscope system. The system can include a second controller configured to control a movement of mechanical stop into a path of the electron beam or into a path of the ion beam to prevent the electron beam or the ion beam from reaching the sample, and the second controller can be configured to control the movement of the mechanical stop in response to a signal from the first controller. The second controller can be logically OFF or logically ON during normal operation of the system. The system can include a plurality of second controllers, each of the second controllers being configured to control a movement of mechanical stop into a path of the electron beam or into a path of the ion beam to prevent the electron beam or the ion beam from reaching the sample, and each of the second controllers can be configured to control the movement of the mechanical stop in response to a signal from the first controller.

In another general aspect, a scanning electron microscope system for imaging a sample can include an electron accelerator configured for generating a primary electron beam for irradiating the sample, an aperture in a mask, where the primary electron beam passes through the aperture when irradiating the sample, a lens configured for focusing the primary electron beam on the sample, a detector configured for detecting a signal of electrons emitted from the sample in response to the irradiation by the primary electron beam, and a means for removing successive surface layers of the sample. The system can include one or more processors configured to control a parameter of the primary electron beam while the primary electron beam irradiates the sample and while the detector detects the signal of electrons, to generate a plurality of images of different surface layers of the sample based on the detected signal from the different surface layers, to vary the parameter when irradiating different surface layers of the sample, including surface layers for which an image is generated based on the detected signal, and to select, based on the plurality of images, a fixed value of the parameter to use for irradiation of subsequent surface layers the sample by the primary electron beam.

Implementations can include one or more of the following features, alone or in combination with each other. For example, the one or more processors can be further configured to fit a curve of an image quality metric for the plurality of images as a function of the varied parameter, and to select the fixed value of the parameter to use for subsequent irradiation of the sample based on the fitted curve. The fixed value can be selected based on the curve having an extremum for as a function of the fixed value. The quality metric can include a focus index (FI) expressed as:

$$FI = \left[\sum_{i=0}^{n-1} \sqrt{(I * S_1 - I * S_2)}\right] / n,$$

where I represents an image of the sample, $S_1$ and $S_2$ represent 2D Gaussian functions of shorter and longer length scales, respectively, than a resolution limit of the scanning electron microscope system, i represents a pixel in the image, and n represents a total number of pixels considered in the image. The different values of the parameter can be selected for different tiles of an image of a surface of the sample. The parameter can include, for example, a focus of the primary electron beam, an astigmatism of the primary electron beam, an aperture alignment of the primary electron beam.

In another general aspect, a method of determining a staining of a sample in a scanning electron microscope image can include creating a first scanning electron microscope image of a stained sample with a scanning electron microscope system, creating a second scanning electron microscope image of an unstained reference sample with the scanning electron microscope system, creating a third scanning electron microscope image of an stained reference sample with the scanning electron microscope system, and quantifying a staining amount of the stained sample based on a comparison of the first image to the second image and based on a comparison of the first image of the stained sample to the third image.

Implementations can include one or more of the following features, alone or in combination with each other. For example, the method can further include creating a fourth scanning electron microscope image of the sample with the scanning electron microscope system without applying a primary electron beam from the scanning electron microscope system to the sample, where quantifying the staining amount is additionally based on a comparison of the first image to the fourth image.

The details of one or more implementations are set forth in the accompanying drawings and the description below. Other features will be apparent from the description and drawings, and from the claims.

BRIEF DESCRIPTION OF THE DRAWINGS

Like reference numerals in the different figures describe like elements in the different figures.

DETAILED DESCRIPTION

Figure 1:
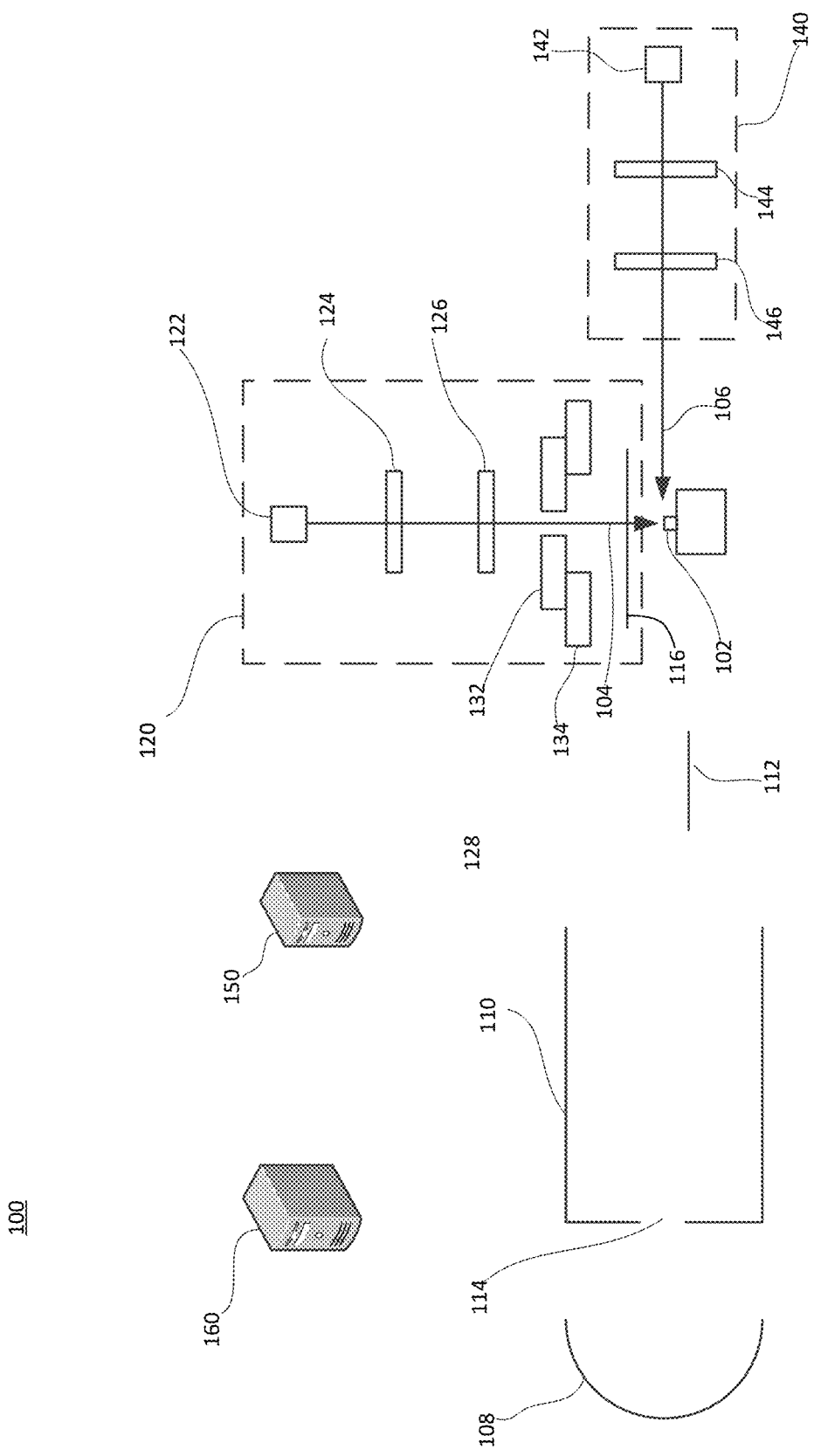
FIG. 1 is schematic diagram of a Focused Ion Beam Scanning Electron Microscopy system.

SEM imaging is generally slower than that of transmission electron microscopy (TEM) for several reasons. First, SEM acquires images pixel-by-pixel in series, whereas TEM acquires all pixels of the image in parallel, with orders of magnitude larger imaging current. Second, SEM detects backscattered or secondary electrons, emitted at a smaller flux than the transmitted electrons measured by TEM. Third, the low SEM landing energy (e.g., less than 2 keV) typically used to reduce the electron penetration depth into the block-face (thus increasing z-axis resolution) can reduce contrast, especially below 800 eV. Fourth, the signal-to-noise ratio (SNR) of a pixel depends on the number of primary electrons devoted to it, which in turn is determined by the beam current. For a resolution of less than 10 nm at low landing energy, the incoming electron beam current can be limited to less than 10 nA, because higher current beams require larger apertures, which are subject to greater spherical and chromatic aberrations as well as Coulomb repulsion, creating unacceptable blur in the beam spot. Finally, post-staining is commonly used in TEM and ATUM-SEM (Automatic Tape-collected Ultra-Microtome Scanning Electron Microscopy) sections to enhance contrast, whereas FIB-SEM must image the block surface without benefit of the extra contrast from post-staining. As a result of all these factors, FIB-SEM requires a lower image acquisition rate than TEM to achieve the same SNR.

The ability to operate a FIB-SEM system for long periods of time is crucial for imaging large volumes. However, along with slow throughput of FIB-SEM, the limited duration of continuous FIB-SEM data acquisition constrains the useable volume. FIB-SEM is destructive and does not allow re-imaging, imposing formidable requirements on system reliability. Interrupts have a direct impact on the total contiguous imaging volume. System drift, routine maintenance, facilities interrupts, or system failures can all terminate a 3D FIB-SEM operation. Focus or beam stigmation of SEM can drift from its optimal settings within 1-2 days, due to environmental or sample stage instability. A pause in the milling/imaging operation is normally needed to correct these drifts and restore image quality. Moreover, a FIB gallium ion source has a lifetime limited to 3-4 months of continuous operation, and requires reheat or 'flashing' every 3 to 5 days. Even without facility or system failures, these regular maintenance events impose hard limits on continuous data acquisition, and thereby the size of contiguous high-quality data sets that can be collected with standard FIB-SEM systems.

Thus, there are many potential interruptions to a FIB-SEM system, with intervals ranging from a few hours to a year. Some of these relate to system reliability, while others are regular maintenance items that are impossible to eliminate, such as FIB source reheat (about every 3 days) and replacement (about every 3 months). Since FIB-SEM image acquisition is destructive, any interrupt can be detrimental. For example, a spike in room temperature may cause the SEM focus to drift, and the FIB beam-pointing position relative to the specimen can change, potentially damaging the sample and sabotaging the continuity required for neural tracing of fine processes across the brain.

Techniques are described herein that enable a reliable and efficient FIB-SEM system capable of imaging large volumes, for example, greater than $10^6$ μm$^3$. These volumes are large enough for studying connectomics, where the fine z resolution can help in tracing of small neuronal processes and speed the tedious and time-consuming human proofreading effort. Even higher resolution can be achieved on smaller volumes. To enable reliable long-term stability, in the event of a potential hazard, the FIB-SEM system can immediately pause to prevent damage and can resume seamlessly after restoration of normal operation. By providing high virtual reliability, this system greatly expands the total imaging volume possible.

FIB-SEM procedures use a focused ion beam to ablate a few nanometers thick layer from the specimen block face, followed by SEM imaging of the freshly exposed surface. These steps cycle continually until an entire 3D volume is ablated and imaged. An advantage of FIB-SEM is the fine z thickness removed with each ablation/milling step, which gives z resolution down to a few nanometers. Many other electron microscopy (EM) techniques yield very different resolutions in the x, y and z directions, and reduced resolution in any one axis can be limiting. For example, details in the xz plane become poorly resolved as the z resolution normal to the xy image planes is decreased. This is particularly problematic in connectomics (the study of neural connectivity), which needs to resolve fine neural processes parallel to the xy imaging plane. Accordingly, a unifying resolution metric can be used in which the resolution of the imaging technique is defined by the worst case resolution in the x, y, or z direction. To elucidate biological structure, it is helpful to render 3D images, without any axial bias, with isotropic resolution. The worst case axial resolution then dictates the appropriate minimal isotropic voxel size for sampling and rendering.

Here, we describe a series of measures that address existing limitations of FIB-SIM, thus transforming FIB-SEM into a tool capable of probing interesting portions of resolution-volume space in imaging. In some implementations, a FIB-SEM system provides multiple layers of error and disturbance protection, including refinements in hardware, software, and utilities, to prevent catastrophic failures, such as an uncontrolled ablation by the focused ion beam during the FIB-SIM imaging process. In some implementations, closed-loop control of the ion beam is used to maintain stability and to protect the sample and the system against damage due to expected and unexpected interruptions of the FIB-SIM imaging process to enable a seamless restart of the imaging cycle after interruptions. In some implementations, the FIB column (e.g., the ion beam of the FIB system) is positioned to be 90 degrees from the SEM column (e.g., the electron beam of the SEM system) instead of the standard 52-55 degrees, which enables a shorter working distance, thus enhancing the imaging quality. In some implementations, the electron detection scheme of the SEM system is modified to capture a large portion of the backscattered electrons, thus providing faster imaging speed with minimal contrast degradation. These modifications can provide a speedy system with overall virtual reliability exceeding that of its individual components. For example, biological volumes as large as 1 million μm$^3$ containing biologically meaningful neuronal elements, such as individual modules in a *Drosophila* brain, can be acquired in a few months. With a newly developed ultrathick partitioning technique, even larger volumes (e.g. an entire *Drosophila* brain) can be subdivided into small pieces and then imaged with multiple FIB-SEM systems running in parallel.

FIG. 1 is a schematic diagram of a FIB-SEM system 100 that includes a scanning electron microscope (SEM) system 120 and a focused ion beam (FIB) system 140. The SEM system 120 includes an electron source/accelerator 122 and one or more focusing lenses 124 and one or more steering elements (e.g., conductive plates) 126 that together produce a primary electron beam 104 that is directed to a sample 102. Secondary electrons emitted from the sample 102 in response to the primary electron beam 104 can be collected and imaged by a detector 128 to produce an image of the surface of the sample 102. For example, images can be generated by processing the signal collected by the detector with a processor to generate an image. In some implementations, the detector 128 can include a plurality of detectors 132, 134 configured for detecting different emitted electron signals. The primary electron beam 104 can be rastered or scanned by the lenses 124 and steering elements 126 across the surface of the sample 102 while the secondary electrons are imaged by the detector 128 in order to build up the image of the surface of the sample 102. The image of the sample 102 shows features of a thin layer of the surface of the sample. In one implementation, one or more detectors 128, 132, 134 can be located between the one or more lenses 124 and the sample 102, in a below-the-lens detection configuration. In one implementation, at least a portion of the one or more lenses 124 can be located between a detector and the sample 102, such that the detector in an in-lens or above-the-lens detection configuration. In some implementations, one or more detectors 128, 132, 134 can be ring shaped and can be located around an axis of the SEM column. In some implementations, one or more detectors 128, 132, 134 can be located off to the side of the axis of the SEM column.

The FIB system 140 can include an ion source/accelerator 142 and one or more focusing lenses 144 and one or more steering elements (e.g., conductive plates) 146 that together produce a FIB beam 106 that is directed toward the surface of the sample 102 and that is used to remove/ablate/mill a thin layer of the surface of the sample 102. In some implementations a gallium ions can be used for the FIB beam. Once the thin layer of the sample has been removed to reveal a new surface of the sample 102, the SEM system 120 can be used again to image the newly revealed surface of the sample 102. Multiple SEM images can be created of each successive surface of the sample 102 that is revealed by the FIB beam. The process of ablation by the FIB beam 106 and imaging by the SEM system 120 can be repeated to image additional layers of the sample 102 that are revealed after ablation of the surface of the sample by the focused ion beam 106. In this manner, a vertical stack of images of the sample 102 can be created, which then can be computationally stitched together to create a three-dimensional image of the sample 102.

In some implementations, the primary electron beam 104 and the focused ion beam 106 can be aligned at substantially right angles to each other. The focused ion beam 106 can be carefully focused and steered, so that the focused ion beam 106 strikes only the top few nanometers of the surface of the sample 102. The energy, focusing, and steering of the focused ion beam 106 and the intensity of the focused ion beam 106 can be controlled, for example, by a processor 150 based on feedback from other components in the system 100, to maintain, over long periods of time (e.g., days, months, years) a desired FIB beam 106 that strikes the sample 102. For example, current values measured on an inner Faraday cup 108, on an annular Faraday cup 110, and on the sample 102 can be used to monitor the performance of the system and as inputs to a feedback system that is used to control the FIB beam.

A beam deflector 112, located downstream of the sample 102 with respect to the FIB ion beam 106 can be voltage biased to steer the FIB beam 106 downstream of the sample 102 in a vertical direction, so as to tune the direction of the beam to pass through one or more mask slits 114 that separate the inner Faraday cup 108 from the annular Faraday cup 110.

A shutter 116 between the sample 102 and components (e.g., the detector 128) of the SEM column can prevent undesired material (e.g., sputtered ions produced by the focused ion beam striking the sample) from entering the SEM column and/or striking components of the SEM system (e.g., lenses of the SEM system, a below-the-lens detector in the SEM system, etc.). In some implementations, the shutter 116 can be a movable mechanical shutter. For example, the shutter can include a movable thin strip of material (e.g., stainless steel) that can be moved in and out of place between the sample 102 and the SEM column. The shutter 116 can be moved into place between the sample 102 and the SEM column, such that while the focused ion beam 106 is on and strikes the sample 102 the components of the SEM column are protected while the SEM system is not being used.

Sample Preparation

Preparation of a biological sample 102 to optimize the sample for serial sectioning by the FIB ion beam can include chemical fixation of the sample 102 based on aldehyde/glutaraldehyde or high-pressure freezing followed by freeze substitution or hybrid approach (e.g. progressive lowering of temperature) were all verified and yielded successful results on FIB-SEM. The sample can be stained with a heavy metal (e.g., osmium) to enhance contrast in SEM images. Because the scattering cross section of the primary electrons scales with the atomic number Z of elements in the sample, and because different tissues may be selectively stained by the heavy metal stain, the heavy metal stain may provide enhanced contrast in SEM images of the sample.

In one example implementation, the head of a five-day-old adult female CantonS G1xw1118 *Drosophila* was cut into 200 µm slices with a Leica VT1000 microtome in 2.5% glutaraldehyde and 2.5% paraformaldehyde, in 0.1 M cacodylate at pH 7.3. The vibratome slice was fixed for a total of 10-15 min, then transferred to 25% aqueous bovine serum albumin for a few minutes, before being loaded into a 220 µm deep specimen carrier and high-pressure frozen in a Wohlwend HPF Compact 01 High Pressure Freezing Machine (Wohlwend GmbH). The brain was then freeze-substituted in a Leica EM AFS2 system in 1% osmium tetroxide, 0.2% uranyl acetate and 5% water in acetone with 1% methanol, for 3 more days. At the end of freeze-substitution the temperature was raised to 22° C., and tissues were rinsed in pure acetone, then infiltrated, and embedded in Durcupan epoxy resin (Fluka). After 48 hours polymerization, the sample was previewed with x-ray microscopy Versa XRM-510 (Xradia®), then oriented and trimmed for FIB-SEM imaging.

In another example implementation, isolated *Drosophila* brain tissues were prefixed in 2.5% formaldehyde and 2.5% glutaraldehyde in 0.1 M phosphate buffer at pH 7.4 for 2 h at 22° C. After washing, the tissues were post-fixed in 0.5% osmium tetroxide in ddH$_2$O for 30 min at 4° C. After washing and en bloc staining with 0.5% aqueous uranyl acetate for 30 min the progressive lowering of temperature (PLT) procedure started from 1° C. when the tissues were transferred into 10% acetone. The temperature was progressively decreased to −25° C. while the acetone concentration was gradually increased to 97%. The tissue was fixed in 1% osmium tetroxide, 0.2% uranyl acetate in acetone for 32 h at −25° C. After PLT and low temperature incubation, the temperature was increased to 22° C., and tissues were rinsed in pure acetone then infiltrated, and embedded in Poly/Bed 812 (Luft formulation).

In another example implementation, after induction of deep anesthesia with sodium pentobarbital (80 mg/kg IP), adult mice (male C57/BL6J, from Charles River) were intracardially perfused with a mixture of 2% glutaraldehyde/2% depolymerized paraformaldehyde, after a brief saline rinse. Brains were removed and postfixed in the same mixture overnight at 4° C. Blocks of tissue including the striatum were cut at 50 µm on a vibratome; sections were collected in phosphate buffer (0.1 M, pH 7.4). Sections were incubated 30 minutes in 0.1% CaCl$_2$, then processed for reduced osmium according to the Graham Knott protocol, then treated with 2% samarium trichloride and 1% uranyl acetate in maleate buffer pH 6.0, prior to dehydration and infiltration in Durcupan resin. Sections were sandwiched between two layers of ACLAR plastic between glass slides, and polymerized 48 h at 60° C. After polymerization, chips from nucleus accumbens were cut out and glued to custom-made copper specimen holders for FIB-SEM imaging.

In another example implementation, *Chlamydomonas reinhardtii* cells were grown heterotrophically on TRIS-acetate-phosphate (TAP) medium in the dark at room temperature. Whole cells were sedimented, lightly fixed with glutaraldehyde (1%) and post-stained with osmium tetroxide, potassium ferrocyanide, and uranyl acetate. The sample was post-fixed prior to dehydration and embedding in hard Durcupan resin, which resin reduced FIB milling artifacts. If samples were already embedded in other resins such as Epon, a thin layer (~5-10 µm) of Durcupan coated on the surface upstream from the FIB milling direction could mitigate the streaking artifacts. The infiltrated and oven cured specimen was then remounted closely onto a metal stud to improve conductivity. After the second curing, the region of interest was trimmed down to form a rectangular post consisting of a block face that is 200×200 µm or less. The trimming could be guided by optical inspection under a microtome and X-ray tomography data, if available. The limited block face size ensured a complete removal of the block face material rather than forming a trench in the sample and improved milling stability by eliminating side-wall effect and back sputtering. A thin layer of conductive material (e.g., 10- to 20-nm gold followed by 50- to 100-nm carbon) could be coated on the trimmed sample using a Gatan 681 High Resolution Ion Beam Coater.

Radiation from the primary electron beam of the SEM system can change the polymer resins commonly used for embedding biological specimens that are imaged by SEM. For example, post-radiated resins can be subject to milling artifacts such as streaks (static line features parallel to the milling direction) and waves (e.g., dynamic uneven milling bands perpendicular to and traveling along the milling direction). The radiation responses of various resins can be very different. For example, acrylic-based resins such as LR White, and regular Epon tend to generate severe streaks and waves, whereas Durcupan can sustain much higher electron beam doses without exhibiting noticeable artifacts. Thus, if an alternate embedding plastic such as Epon is needed, the milling artifacts can be mitigated by coating the front face of the sample, (i.e., the face facing the ion beam) with 5-10 µm layer of Durcupan. Nevertheless, when milling layers of the sample 102 with the FIB beam, for layers less than about 10 nm, the FIB beam milling can have difficulty milling more than 100 µm in the beam direction on Durcupan resin (representing a nominal SEM dose of 30 electrons per $nm^3$). To permit large volume imaging using FIB-SEM, an ultra-thick partitioning method has been developed, in which the sample is diamond cut into thick slabs (e.g., 20-25 µm thick), which are then 3D imaged with the FIB-SEM process. This not only removes this potential hard barrier for large volume acquisition, but also enables high-throughput parallel 3D imaging with FIB-SEM. These 20-25 µm thick slabs also can use the Durcupan coating on the front side.

Figure 2:
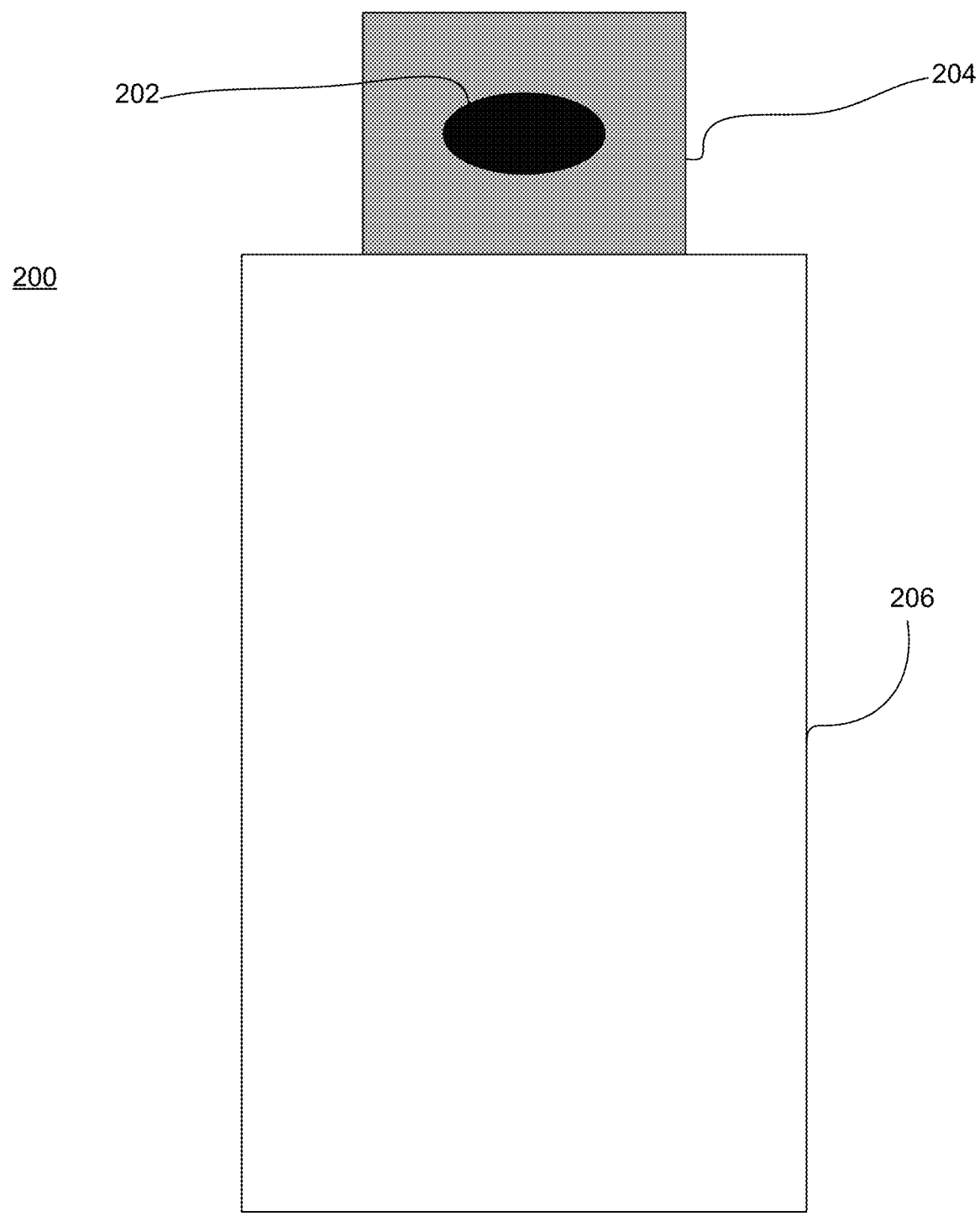
FIG. 2 is schematic diagram of a sample in preparation for imaging.

FIG. 2 is schematic diagram of a sample 202 in preparation for imaging. In some implementations, the sample 202 can be embedding in a resin 204, for example, and epoxy resin, such as Epon or Durcupan. The embedded sample 202 can be mounted on top of a conductive metal post 206. The metal post 206 can be in electrical contact with the metal-stained sample 202 to facilitate charge dissipation from the sample 202 when the sample is irradiated by the FIB ion beam or the primary electron beam.

Figure 3:
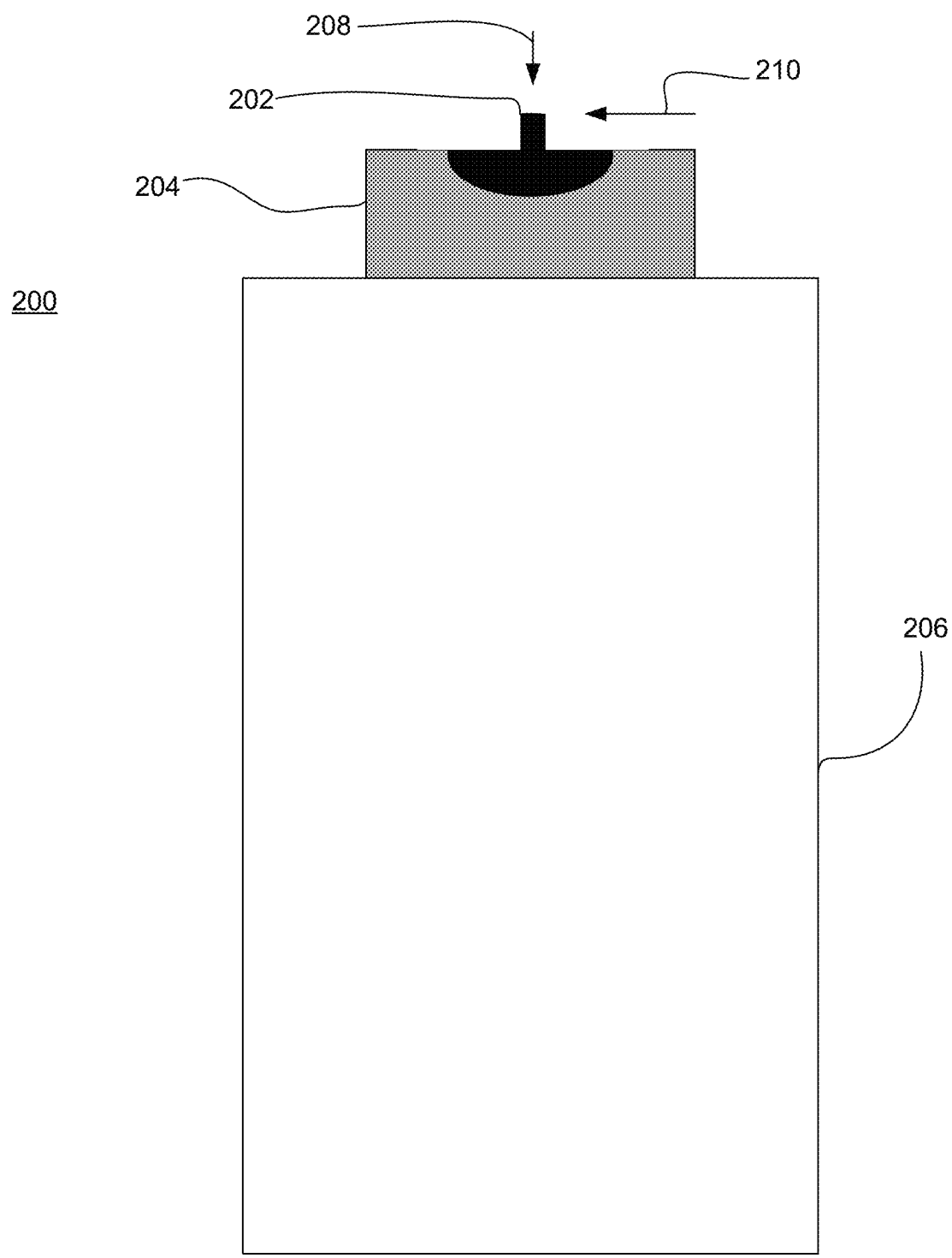
FIG. 3 is another schematic diagram of a sample in preparation for imaging.

FIG. 3 is another schematic diagram of a sample in preparation for imaging, showing that a portion of the resin 204 has been trimmed away from the sample 202 to reveal a vertical post of the sample for milling by the FIB beam, which can impinge on the sample in direction 210, and for SEM imaging in response to irradiation by a primary electron beam from the SEM system, which can impinge on the sample in direction 208. In some implementations, the vertical post of the sample 202 can be trimmed to a width of <500 µm and a depth of <200 µm in the direction of the ion beam. With this configuration, the FIB ion beam can mill the top of the post but not imbed significantly into the sample. A thin conductive coating around the outside of the trimmed sample and the remaining resin (e.g., with 10 nm sputtered gold and 100 nm sputtered carbon precision etching and coating system) can provide further charge dissipation from the sample 202.

Closed-Loop Control for FIB Milling

The precision sectioning of the sample 102 by the FIB ion beam 106 is a very unforgiving aspect of FIB-SEM. Loss of control of the focused ion beam 106 can destructively ablate as much as a full micrometer of material from the sample 102 without the associated imaging, thereby destroying the continuity of large data sets with potential loss of months of invested imaging effort. Even small instabilities can nucleate waves and curtains of non-uniform milling. Beyond ensuring stable ion beam parameters such as current, stigmation, and focus as intrinsic aspects of the ion column, but also to ensure reliability, a feedback mechanism is provided to regulate the ion beam milling height with respect to the sample 102.

In one implementation, a feedback scheme can capture, in a Faraday cup 108, the portion of the focused ion beam 106 that does not hit the sample 102, and a current signal due to the non-occluded ion beam current on the Faraday cup 108 can be measured. The current signal can be provided to a system control computer 150 that can subtract the non-occluded beam current from the total beam current as measured in a Faraday cup located upstream of the sample, providing an estimate of the total beam current impinging on the sample. When the system control computer 150 detects an increase in the current impinging on the sample 102, the control computer 150 can control the ion beam (e.g., by controlling the ion flux from the source 142 or by controlling, though the lenses 144 and steering elements 146, the focus and/or direction of the beam) to raise the beam (to lessen the occlusion). Likewise, a detected decrease in beam current impinging on the sample 102 can cause the system control computer 150 to lower the FIB ion beam 106 into the sample 102, thereby increasing the milling rate of the sample 102 while reducing the current on the Faraday cup 108.

In another implementation, the inner Faraday cup 108 can capture the non-scattered ion beam 106, but with a smaller acceptance slot consistent with the beam spread and horizontal scanning of the beam, while a second annular Faraday cup 110 can capture the more widely scattered ions and milled sample material. The current measured by the annular Faraday cup 110 can provide a more direct measure of the milling rate of the sample 102 and can be used as an input signal to the control computer 150 in a feedback scheme to control the FIB ion beam 106 that mills the sample 102.

In another implementation, a current that is generated on the sample by the FIB ion beam 106, which should be proportional to the milling rate, can be measured on the sample. In some implementations, a current preamplifier that could be voltage biased (e.g., to ±800 volts) can be used to measure these currents on the sample 102 over a wide range of sample bias voltages. The system control computer 150 can monitor parameters (e.g., currents) measured by the inner Faraday cup 108, the annular Faraday cup 110, the sample 102, as well as other measured system parameters (e.g., the main power supply, cooling water temperature, environmental temperature, etc.) and can adjust parameters of the ion beam and the SEM beam to ensure that the measured parameters remain within specified ranges to protect the sample and the system.

When feedback is based on the inner Faraday cup current, operation of the feedback scheme is relatively simple, but variations in the ion source emission properties, such as beam shape generally are not compensated and can induce a non-uniform milling rate. To some extent this can be corrected with post-processing software to normalize an estimated milling increment in a direction normal to the surface of the sample 102. A measurement of the current on the sample 102 is a composite of multiple components, including not only the impinging positive milling ions, but also secondary electrons that are generated, as well as any charge that the milled sample atoms remove. As a result, the value and sign of the feedback based on the sample current can be difficult to determine, and under certain beam shape condition can be even close to zero, potentially leading to milling instabilities. Feedback based on the current measured on the larger annular Faraday cup 110, which captures scattered Ge ions and any charged ions milled from the sample can yield a relatively uniform milling rate that exhibits only minimal sensitivity to changes in the gallium source emission profile and ion currents. In some implementations, feedback based on the inner Faraday cup current can be used to continuously control the ion beam over short timescales (e.g., less than a minute, less than a second, less than 100 milliseconds, less than 10 milliseconds), and additional bounded checks on the other currents (e.g., the annular Faraday cup current, the sample current, etc.) can be used to allow continuation of milling.

Figure 4:
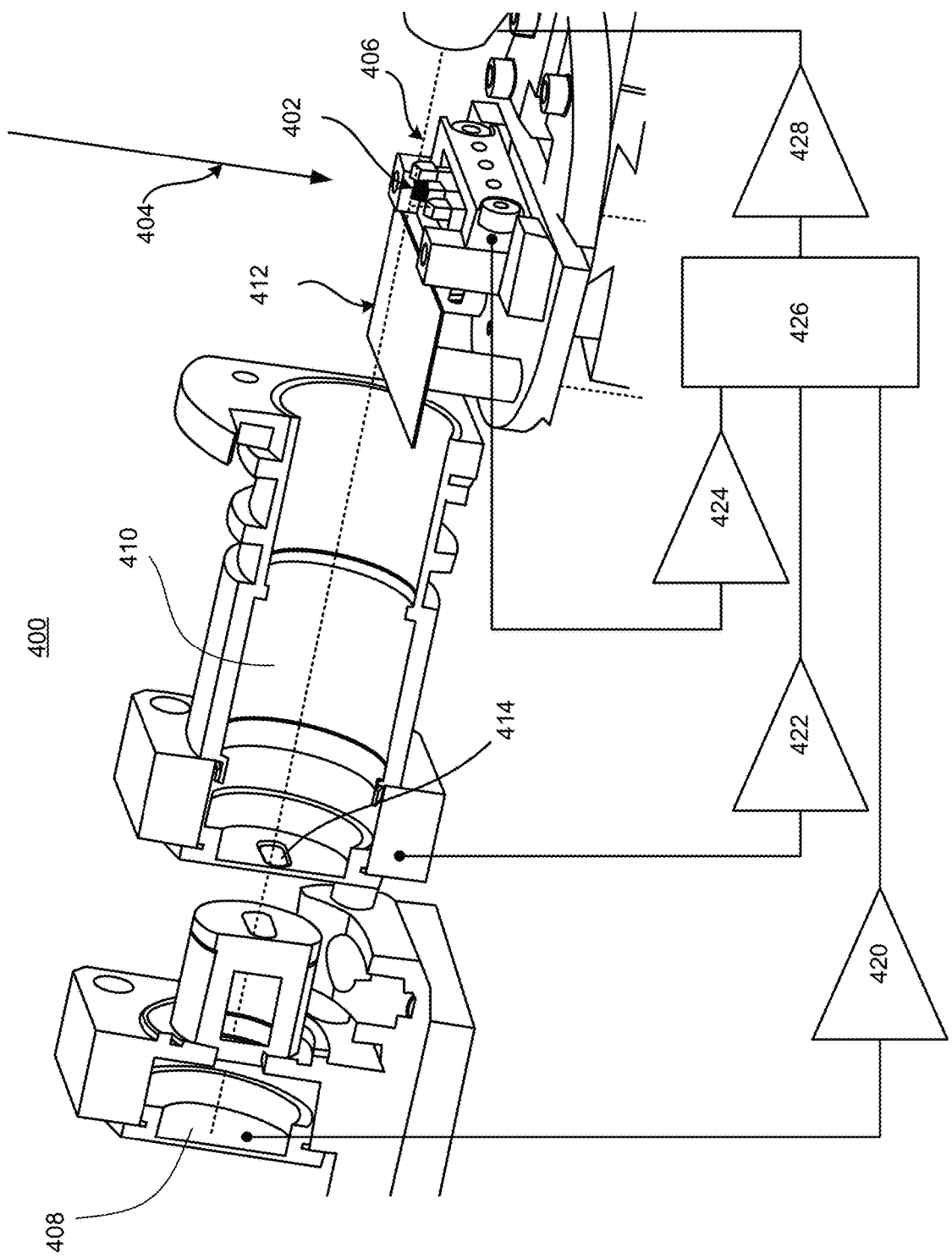
FIG. 4 is another schematic diagram of a Focused Ion Beam Scanning Electron Microscopy system.

FIG. 4 is another schematic diagram of a Focused Ion Beam Scanning Electron Microscopy system 400 that includes a sample 402, which can be milled by an ion beam 406 and imaged by a primary electron beam 404. The system can include a inner Faraday cup 408 located at the end of the ion bema path and an annular Faraday cup 410 that can collect scattered ions and ablated sample material. A deflector plate 412 can steer the ion beam downstream of the sample relative to a slit 414 in the annular Faraday cup 410, so that the beam can enter the inner Faraday cup after passing through the slit.

Currents on the inner Faraday cup 408, the annular Faraday cup 410, and the sample 402 can be amplified by amplifiers 420, 422, 424, respectively and provided to a processor 426 that receives and monitors the currents to ensure stable and reliable operation of the system 400. Based on the signals provided to the processor 426, the processor can provide a signal (e.g., through an amplifier 428) to the FIB system that produces the FIB beam 406. Variations in the signals provided to the processor 426 from the currents on the Faraday cups 408, 410 and the sample 402 can cause corresponding variations in the signal provided to the FIB system to maintain a stable, reliable operation of the system.

In another implementation, a current on the shutter 116 can be monitored, and a signal representing the current on the shutter can be provided to the processor 426 as an additional signal with which provide a feedback signal to FIB system to ensure stable and reliable operation of the system 400.

Prompt Pausing and Seamless Restart

To foresee upcoming interrupts and react proactively, the health of the FIB-SEM system can be monitored in real time by the system control computer 150, which records machine and environment parameters, to generate trend charts. Statistical process control methods can be used to identify any excursions beyond normal limits, and to alert an operator (e.g. through email) or to automatically pause the operation of the system 100. Parameters monitored included but not limited to room temperature, sample current during FIB milling and SEM imaging, FIB beam position relative to the sample, charged particle detectors, image X-Y shift, image focus index, and feature changes between adjacent frames of an image that is recorded by the SEM system 120.

A prompt pause of the system 100 prevents damage to the sample 102, but to resume the operation seamlessly after system restoration is challenging. A difficult problem is how to re-aim the FIB beam with nanometer precision back to its position on the sample 102 just before the pause, to avoid over- or under-milling of the sample. In addition, during repeated cycles of milling and imaging, steady states of charge and temperature can be established on the block face of the sample 102, and these steady states can require specific focus and stigmation settings for the primary electron beam 104 from the SEM system 120 to operate as planned. These imaging parameters of the primary electron beam 104 are optimized for the steady state of the system, and thus would not be suitable for a cold start. However, by utilizing the closed-loop control of the FIB system 140 described above it is possible to detect and control the positioning of the FIB beam 106 relative to the block face of the sample 102 with no delay and overhead, thus greatly reducing the uncertainty for FIB re-engagement, ensuring consistent milling at all times. Furthermore, in some implementations, when the system deviates from the steady state upon a restart, the focus and stigmation changes of the primary electron beam of the SEM system can correlate to the lateral shifts of the image of the sample, in which case subsequent images of the sample obtained after a restart can be registered to adjacent, previously-generated images.

Dead Man's Switch to Protect Against System Failure

To further protect the sample and the system 100 against failures by the system control computer 150 and by feedback loops controlled by the system control computer 150, a dead man's switch can be implemented to shut off the ion and electron beam currents to the sample 102 in the event of such a failure. In one implementation, a dead man's switch control computer 160 (e.g., a National Instrument CompacRIO platform computer) can monitor signals that are provided by other components of the system (e.g., voltage signals used to open or close the SEM shutter 128 during operation, currents generated by the SEM imaging, currents generated by the FIB milling, a continuously provided "heart beat" signal from the system control computer 150, etc.). The dead man's switch control computer 160 can be used to control the operation of control valves in the SEM system 120 and the FIB system 140 to prevent any ion or electron beam currents from reaching the sample 102 in the event that a signal monitored by the dead man's switch control computer 160 is out of specification.

For example, the dead man's switch control computer can control a current that is provided to solenoids that control the state of valves or shutters in the SEM and FIB beam columns. In one example implementation, when the signals monitored by the dead man's switch control computer 160 are within specification, the dead man's switch control computer 160 can power the solenoids to open the valves/shutters (that are normally closed) in the SEM system 120 and the FIB system 140 to allow data to be acquired. The dead man's switch 160 can be logically "ON" in this case. However, when one of the monitored signals is not within specification, the dead man's switch control computer 160 can cease to provide current to the solenoids, such that the valves/switches close, such that the ion and electron beam currents are prevented from reaching the sample 102.

In another example implementation, the valves/shutters can be normally open, such that data acquisition can proceed while the dead man's switch 160 is logically "OFF." However, when at least one of the signals monitored by the dead man's switch control computer 160 is not within specification, the dead man's switch control computer 160 can control the operation of the solenoids to close the valves/shutters in in the SEM system 120 and the FIB system 140 to prevent ion and electron beam current from reaching the sample 102.

Multiple dead man's switches 160 can be used to control the values/shutters in the SEM system 120 and the FIB system 140, such that when any one of the dead man's switches 160 detects a signal that is not within specification, the valves/shutters are closed and ion and electron beam current is prevented from reaching the sample 102. Having such redundant dead man's switches can enhance the protection of the sample, in the event that one of the redundant switches fails.

Thus, the dead man's switch control computer 160 protects the sample from damage, even in the event of a failure of the system control computer 150 or one of the feedback loops that the system control computer maintains.

SEM Signal to Noise Ratio

SEM imaging can be the rate-determining step in a FIB-SEM procedure, since the milling procedure of the FIB system 140 is generally faster than the imaging procedure of the SEM system. To understand the limits of fast imaging the signal to noise ratio, SNR, of the image can be considered. The signal can be the number of electrons that are detected from an osmium or heavy metal rich stained membrane, Nm, minus the number of electrons detected from the unstained cytosolic region, Nc. (both Nm and Nc are signals in a pixel of an electron micrograph). These numbers scale with the number of primary beam electrons, Np impinging on the sample 102. In some implementations, when the signal of the stained membrane over unstained cytoplasm (Nm−Nc) is much less than (Nm+Nc), the average number of detected electrons Ne− is about (Nm+Nc)/2. The noise as determined by statistics of the limited number of electrons collected with one pixel is given by sqrt(Ne−). The ratio of signal (of membrane over cytoplasm) to average image noise, SNR, can be approximated as:

SNR=(Nm−Nc)/sqrt(Ne−)=(Nm−Nc)/sqrt((Nm+Nc)/2), which is proportional to the square root of the number of electrons associated with the pixel. This in turn scales with the primary beam current, Ip, times the dwell time t of a pixel, Np=Ip*t.

In-Line Image Auto-Optimization

During extended image acquisition, SEM focus, stigmation, and aperture alignment need to be optimized periodically to correct drift of various components. Traditionally, these optimizations were performed manually off-line, causing interrupts to the continuous milling and imaging process. However, such an approach not only increases overhead, but also introduces further errors by disturbing the steady state of milling and imaging cycles.

To overcome these issues, the SEM image of the sample can be automatically optimized in-line, while the milling and imaging processes proceed. First, a "focus index" based on the strength of the highest spatial frequency components can be calculated to assess the focus quality for each SEM image acquired from the sample 102. The original image can be smoothed by shorter and a longer length scales that straddle the resolution limit of the SEM system. The totaled root mean square pixel-to-pixel difference between these two smoothed images can be assigned to the original image as a focus index. For example, the focus index can be defined as $$FI = \left[\sum_{i=0}^{n-1} \sqrt{(I * S_1 - I * S_2)}\right] / n,$$

where the original 2D image I is smoothed by 2D Gaussian functions of a shorter ($S_1$) and a longer ($S_2$) length scale that straddles the resolution limit. In one implementation, standard deviation values for Gaussian distributions $S_1$ and $S_2$ can be 1 and 4 pixels, respectively.

A higher focus index indicates more high spatial frequency content, and therefore a better-focused image. The focus index value depends upon the highest spatial frequency sample features, the actual focus of the electron beam spot, and the signal intensity. However, in comparing neighboring frames in a 3D FIB-SEM image stack, there were minimal variations in either sample features or signal intensity, so the focus index is conveniently sensitive to the beam spot size.

Figure 6A:
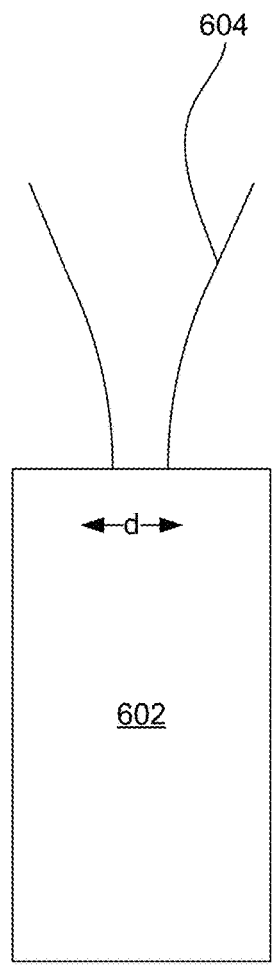
FIGS. 6A, 6B, and 6C are schematic diagrams of a primary electron beam irradiating a sample.
Figure 6B:
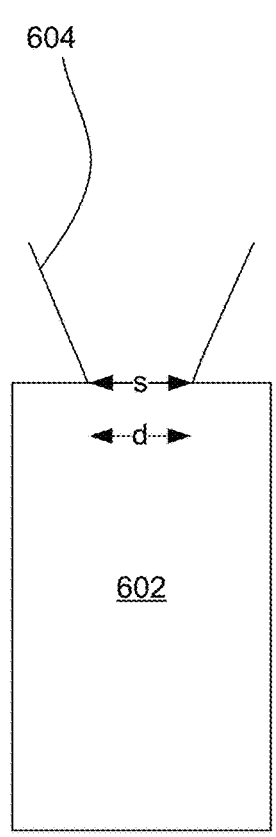
Figure 6C:
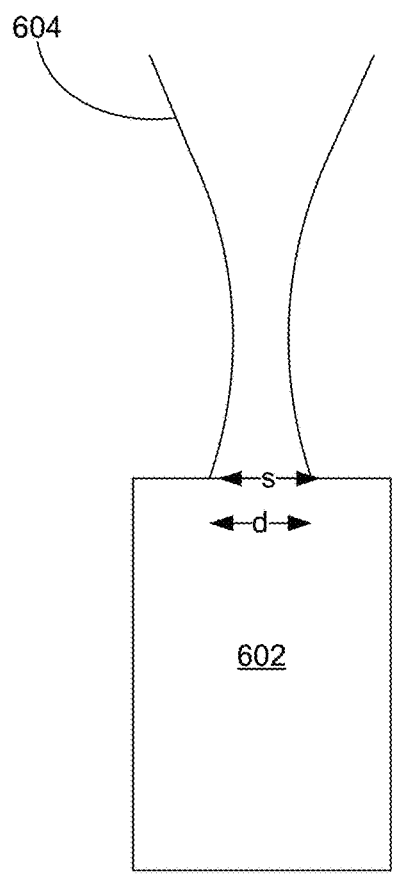

Thus, to initiate an in-line auto focus procedure, a series of SEM images of sequential layers of the sample can be taken a small distance over- and under-focus from a current value. For example, to optimize a focal length as a parameter of the primary electron beam while frames of the 3D image stack are acquired, a first surface layer of the sample can be imaged with a first focus of the primary electron beam. FIG. 6A is schematic diagram of a primary electron beam 604 irradiating a sample 602, where the spot size (s) of the primary electron beam on the surface of the sample is less than the resolution limit (d) of the SEM system (e.g., as defined by a pixel size of images acquired by the SEM system). Then, a thin surface layer can be removed from the sample, and a second surface layer of the sample can be imaged but with an under focused primary electron beam that can cause the spot size of the electron beam on the sample to be larger than the spot size of the beam in FIG. 6A, for example, close to the resolution limit of the system. FIG. 6B is schematic diagram of a primary electron beam 604 irradiating a sample 602, where the spot size (s) of the primary electron beam on the surface of the sample close to the resolution limit (d) of the SEM system. Then, another thin surface layer can be removed from the sample, and a third surface layer of the sample can be imaged but with an over focused primary electron beam that again can cause the spot size of the electron beam on the sample to be larger than the spot size of the beam in FIG. 6A, for example, close to the resolution limit of the SEM. FIG. 6C is schematic diagram of a primary electron beam 604 irradiating a sample 602, where the spot size (s) of the primary electron beam on the surface of the sample is close to the resolution limit (s) of the SEM system. Thus, a sequence of images is obtained by varying a parameter (e.g., the focal length) of the primary electron beam that is used to generate a 3D image of the sample.

A parabolic curve fit to the focus index vs. the value of the varied focus parameter then can be used to extract the optimal focus setting for an image, maximizing the focus index. Upper and lower bounds of the optimal setting can be specified to prevent outliers. This derived optimal setting for the focus parameter then can be applied to subsequent images, with a correction for the anticipated z-axis removal from milling incorporated into the target focus setting. Using the same basic approach, other parameters of the primary electron beam (e.g., stigmation and aperture alignment settings for x and y axes) also can be optimized. After the system reaches steady state for milling and imaging (typically within 1-2 hours), a few iterations of the auto-focus, stigmation, and alignment routine can be used to optimize SEM imaging conditions. To continually correct subsequent slow drifts of the system, the auto-focus routine can be automatically triggered (e.g., by the computer 150) at regular or irregular intervals (e.g., every 200 frames or every few hours). This infrequent sampling and almost imperceptible defocus can minimize any possible compromise in the data quality, and it does not cause any throughput overhead or additional radiation damages compared to other approaches.

In some implementations, parameters of the SEM system can be optimized with this procedure for different portions of an image of a layer of the sample. For example, a surface layer of the sample can be divided into multiple tiles, and one or more SEM parameters can be independently optimized for different tiles of the surface layer.

Although this process of in-line image optimization is described above in the context of using a FIB system as the means for removing successive surface layers of the sample, other means of removing surface layers also can be used. For example, a diamond knife system can be used to remove successive surface layers with an ultra sharp and thin knife (e.g., made of diamond). In another implementation, a gas cluster ion beam (GCIB) system could be used as a means to remove successive surface layers of the sample, in which a beam of an ionized cluster of atoms, rather than a beam of individual ionized atoms, is used to mill away a surface layer of the sample 102.

Multiple Magnifications at User-Selected Intervals

In some cases, multiple resolutions can be used to resolve different features in an image stack and to provide context for an image feature. One option is to image the entire volume using the highest resolution needed. However, it can be more efficient to change imaging resolution at different locations. For example, in a sample of fly brain, small and dense neuropil structures are surrounded by large cell bodies. Instead of imaging everything at high resolution, only the smaller regions of interest containing the neuronal connections could be imaged at high resolution, while the larger area image(s) could be acquired more quickly at lower x, y, and z resolution.

FIB-SEM Column Configuration

In many existing FIB-SEM systems, the SEM and FIB columns are mounted at an angle of 52-55 degrees with respect to each other. This configuration allows a wide range of applications, but is suboptimal for 3D volume imaging. Because the milled block face is not perpendicular to the SEM column, the focus or working distance of the scanning electron beam needs to be dynamically adjusted as it scans across the tilted surface, which not only affects the SEM image quality near the top and the bottom edges, but also constrains the flexibility of rotating a typical rectangular scanning area to accommodate sample shapes. Moreover, the coincident point between the SEM and FIB beam is limited to ~5 mm due to space constraints of the two columns. The resulting long working distance leads to signal reduction from the smaller solid of collection (especially using the in-column lens detection scheme) and resolution degradation from the poorer focus at longer working distance.

To overcome these difficulties, the column of the FIB system 140 can be mounted perpendicular to the column of the SEM system 120. This combined system permits a working distance of ~3 mm, producing superior SEM images with greater flexibility. Because the column mounting orientation can affect the FIB emission characteristics, closed-loop control of the FIB beam 106 can be used to ensure milling stability. Also, in this configuration, the bottom of the SEM column can be contaminated by FIB-sputtered material over time due to its close proximity of the SEM column to the sample 102, thus reducing image quality and affecting system stability especially after a system pause, with contamination of the SEM column from FIB-sputtered material being further accelerated with shorter working distance. Accordingly, a mechanical shutter 116 installed between the sample 102 and the bottom of the SEM column can shield the SEM column during FIB milling of the sample. The shutter 116 can be moved into the path between the SEM column and the sample 102 during FIB ion beam milling cycles to keep the bottom of SEM column debris-free even after hundreds of thousands of milling cycles and can be removed from the path between the SEM column and the sample 102 during SEM imaging cycles.

SEM Artifact Reduction

Electrons detected by the detector 128 can include both energetic backscattered electrons and lower energy but more numerous secondary electrons. In some implementations the detector can include two or more detectors that are configured for selectively detecting the different signals (e.g., the backscattered electron signal and the secondary electron signal). For example, the SEM system 120 can include, an energy-selective backscattered electron detector (EsB) 132 and an in-column secondary electron detector 134. Because the backscattered electron signal provides clean and excellent material contrast, it is often used for FIB-SEM applications. However, a larger solid angle of the secondary electrons also can be collected in the secondary electron detector 134 with potentially faster imaging. Unfortunately, the secondary electrons can contain noise terms, and artifacts of charging, topography, burn marks, and non-uniform work function that can affect the backscattered electron signal to a lesser degree.

Some of these artifacts are sensitive to the material used. For example Epon, a common epoxy embedding compound, can develop streaks and uneven milling especially downstream (in the milling direction) on the milled surface. Alternate epoxy embedding resins such as Durcupan can be less prone to such streaks and waves, such that streaks are relatively absent, at least over the initial portion of the sample that is milling, although they can develop further downstream (e.g., 20 µm downstream) in the milling direction when imaging with a dose>50 electrons per $nm^3$. If the streaks are sufficiently mild and occupy only a small part of Fourier space, they can be removed by applying a masked Fourier filter that removes the spatial frequencies of the streaks.

To address these issues, a positive voltage bias can be applied to the sample 102, which can effective to filter out low energy secondary electrons from the secondary electron detector 134, while maintaining a larger collection angle for the backscattered electrons. Images generated from the secondary electron signal collected by detector 134 when the sample 102 is positively biased can show a reduction or elimination in the rectangular electron burn spot and can appears similar to images generated from the backscattered electron signal collected by detector 132, but with noticeably improved SNR. The positive voltage bias enables the secondary electron detector 134 to offer much improved material contrast, with a ~5-10× gain on electron counts compared to the backscattered electron detector 132 alone. Such a bias also can reduce or remove mild streak artifacts due to the FIB beam milling that appear a short distance (e.g., 20 µm) downstream from the front (upstream) surface of the milled surface. Moreover, the signal from both detectors 132, 134 can be combined through simple weighted average to further lower shot noise without degradation in image contrast.

The value of the positive bias applied to the sample can be optimized for a number of different parameters and conditions. We tested bias voltages over a range of values, while adjusting the primary electron beam energy to maintain a fixed landing energy of the primary electrons on the sample of 1.2 keV, with the distance between the sample and the electron column fixed at 3 mm. In our tests, the total electron counts measured on the secondary electron detector 134 increased as the bias voltage increased from −600 V, reaching a broad maximum between 0 and +400 V, before a sharp drop-off at +600 V and beyond. The initial increase of collected electrons was likely due to a lensing effect near the column entrance that allows more electrons to reach the ring-shaped secondary electron detector 134. The sharp decrease of electron signal with bias voltage above +600 V indicated the threshold of secondary electron removal, which is consistent with the formation of a ~50 eV axial potential barrier that is formed by proximity to an +8 kV electrode together with a grounded end cap and thus capable of blocking secondary electrons to the secondary electron detector 134. As expected, the threshold is a function of the distance between the sample and the electron column, where a shorter working distance between the sample and the electron column requires higher bias voltage to effectively filter out secondary electrons. The main advantage of the backscattered electron detector 132 is the higher contrast (e.g., of ~40 to 50%) compared that of the secondary electron detector 134 (e.g., of to ~10%). However, the total number of electrons detected by the backscattered electron detector 132 is only a small fraction (around 1% or less) of those recorded by the secondary electron detector 134. Adding a positive bias voltage of (e.g., of about +600 V) can significantly increase the contrast of the signal from the secondary electron detector 134 (e.g., to around 20%), while the SNR of the signal remains high (e.g., above 10 or about twice of that provided by the backscattered electron detector 132).

Thus, a positive voltage bias on the sample 102 can provide a simple and effective alternative to generate strong contrast images similar to those generated from signals measured by the backscattered electron detector 132, but being generated from signals measured by the secondary electron detector 134. The resulting images, obtained from signals collected with a positive sample bias, can be relatively free of artifacts, with sufficient contrast and SNR for high quality automatic segmentation of neural tissue. With this approach, it can be possible to increase throughput significantly (e.g., by a factor of 10 or more), as compared with generating SEM images with an unbiased sample. However, when the steady state FIB-SEM imaging generated only limited and tolerable artifacts (e.g. streak artifacts, which could be removed by a simple mask on the Fourier transform), the 0 to +400 V sample bias and the larger aperture of the InLens detector gave the best signal-to-noise and throughput performance.

Calibration of Sample Osmium Concentration

To determine an osmium, or other heavy metal, concentration in a sample an SEM image of the sample can be calibrated against SEM images of reference samples whose composition is known. For example, reference compounds can be used of pure gold, epoxy (the embedding plastic used for the biological samples), and Tetrakis(triphyenylphosphine) platinum $Pt[(C_6H_5)_3P]_4$, a compound with a known 16% density by weight of platinum (atomic number $Z=78$) and which can be expected to scatter electrons similarly to osmium ($Z=76$) stained lipids. For pure gold, 40% of the incoming electrons are backscattered. For epoxy, $H_{25}C_{21}O_5$, the absence of high Z atoms reduces backscattering to a base of 8.3% of the incoming beam. The 16% weight loading of Pt in the reference $Pt[(C_6H_5)_3P]_4$ compound boosts the backscattered fraction to 10.4%.

Figures 5A, 5B:
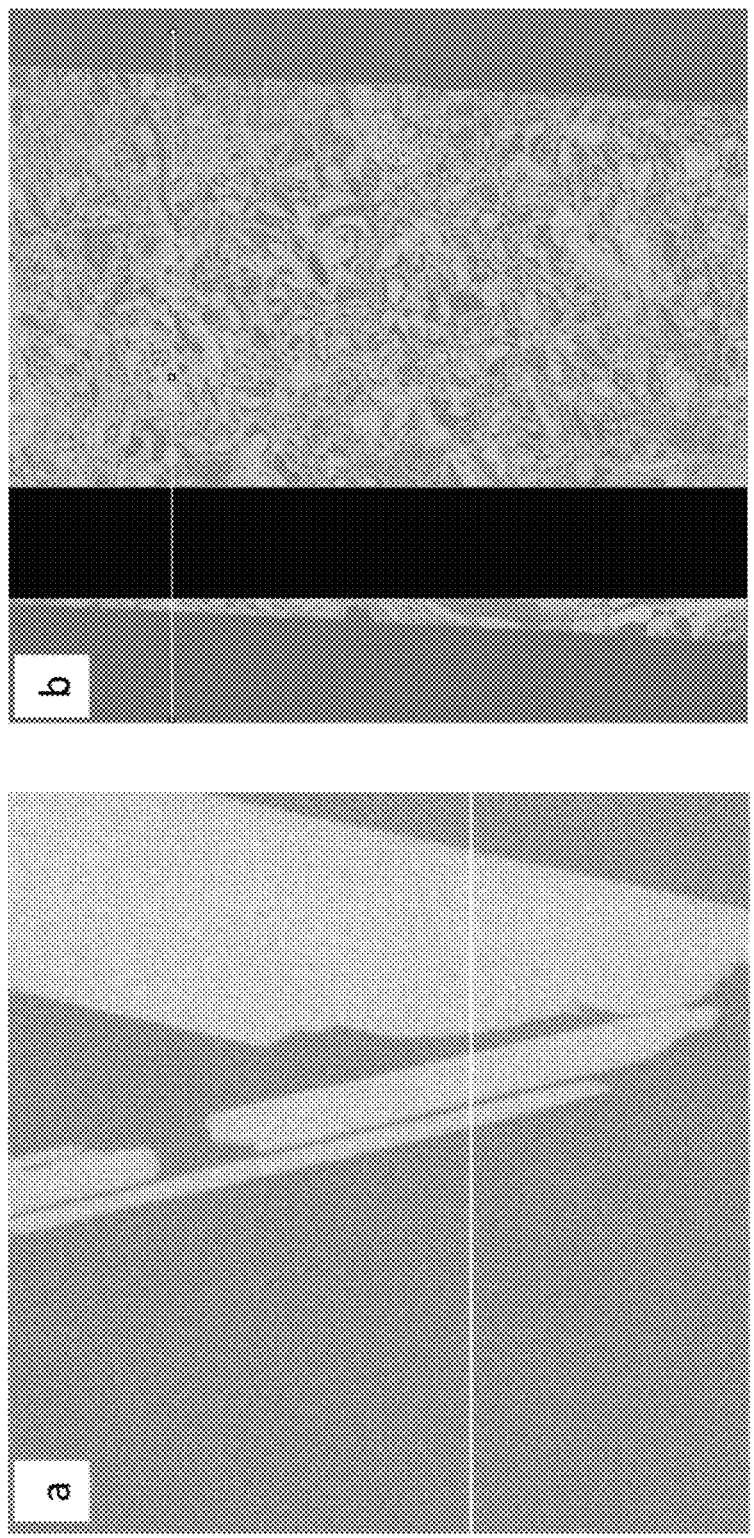
FIGS. 5A and 5B are electron micrograph images of reference samples compared with neuropil.

A quantitative comparison between these reference samples and neuropil is shown in FIGS. 5A and 5B. The electron micrograph in FIG. 5B shown an image of an osmium-stained sample to the right of a black vertical bar, which corresponds to a signal received with a primary electron beam is blocked from reaching the sample. The electron micrograph of the osmium-stained sample has about the same signal and contrast as an electron micrograph of Pt Tetrakis in epoxy, shown at the right side of FIG. 5A, suggesting that the neuropil sample has the same 16% by weight heavy metal fraction as the Pt Tetrakis reference sample.

For a representative estimate of stained plasma membrane signal we assume a composition close to one osmium atom for each molecule of lipid ($X_{Os}=1$, stained). Using lecithin, a common membrane lipid with a composition of $C_{41}N_1O_8P_1H_{78}Os_{1.0}$, as a representative lipid would predict 23% by weight of the osmium stain. The measured signal is almost identical to the $Pt[(C_6H_5)_3P]_4$ with its 16% Pt by weight. This is consistent with $Os_{0.7}$, ($X_{Os}=0.7$), which is a reasonable value given the complexities that determine staining concentration of heavy metal stain in a true cell membrane.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, solid state drives, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT) or liquid crystal display (LCD) or light emitting diode (LED) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback or notification, e.g., email or text message; and input from the user can be received in any form, including acoustic, speech, or tactile input, email or text message.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the implementations.

What is claimed is:

1. A microscopy system for imaging a sample, the microscopy system comprising:
a focused ion beam system configured to direct a focused ion beam onto a sample;
a scanning electron microscope system configured to direct an electron beam onto the sample; and
a plurality of charged-particle detectors, each detector being configured to monitor an electrical current on the detector, wherein the plurality of charged particle detectors includes a movable shutter located between the sample and the scanning electron microscope system, the shutter being configured to be moved automatically into a position between the sample and the scanning electron microscope system, so that when the electron beam is not irradiating the sample the shutter is positioned between the sample and the scanning electron microscope system and blocks sputtered ions produced by the focused ion beam directed onto the sample from entering a column of the scanning electron microscope system; and
a control computer configured to receive a plurality of signals indicative of the electrical currents on the plurality of charged particle detectors and configured to control automatically properties of a focused ion beam produced by the focused ion beam system in response to the received signals when the shutter is positioned between the sample and the scanning electron microscope system.

2. The system of claim 1, wherein the control computer is configured to automatically prevent a focused ion beam produced by the focused ion beam system from striking the sample in response to at least one of the signals of the plurality of signals having a value that is outside a range of predetermined values.

3. The system of claim 1, wherein the control computer is configured to automatically control the focused ion beam milling rate in response to at least one of the signals from the plurality of charged particle detectors.

4. The system of claim 1, wherein the plurality of charged particle detectors includes an inner Faraday cup configured to capture non-scattered ions produced by the focused ion beam system, and an annular Faraday cup configured to capture ions produced by the focused ion beam system and scattered by the sample.

5. The system of claim 1, wherein the plurality of charged particle detectors includes the sample.

6. The system of claim 5, wherein the sample is maintained at a positive voltage bias that is selected to reject electrons below an energy threshold from entering the scanning electron microscope system.

7. The system of claim 1, further comprising a switch configured to control a movement of a mechanical stop into a path of the electron beam or into a path of the ion beam to prevent the electron beam or the ion beam from reaching the sample, wherein the switch is configured to control the movement of the mechanical stop in response to a signal from the control computer.

8. The system of claim 1, further comprising a plurality of switches, each of the switches being configured to control a movement of a mechanical stop into a path of the electron beam or into a path of the ion beam to prevent the electron beam or the ion beam from reaching the sample, wherein each of the switches is configured to control the movement of the mechanical stop in response to a signal from the control computer.

9. The system of claim 1, wherein the scanning electron microscope system includes a focusing lens and a detector located between the focusing lens and the sample.

10. The system of claim 1, wherein the scanning electron microscope system includes:
an electron accelerator configured for generating a primary electron beam for irradiating the sample;
an aperture in a mask, wherein the primary electron beam passes through the aperture when irradiating the sample;
a lens configured for focusing the primary electron beam on the sample;
a detector configured for detecting a signal of electrons emitted from the sample in response to the irradiation by the primary electron beam; and wherein the system includes:
one or more processors configured to:
control a parameter of the primary electron beam while the primary electron beam irradiates the sample and while the detector detects the signal of electrons,
generate a plurality of images of different surface layers of the sample based on the detected signal from the different surface layers,
vary the parameter when irradiating different surface layers of the sample, including surface layers for which an image is generated based on the detected signal, and
select, based on the plurality of images, a fixed value of the parameter to use for irradiation of subsequent surface layers of the sample by the primary electron beam.

11. The system of claim 10, wherein the one or more processors are further configured to:
fit a curve of an image quality metric for the plurality of images as a function of the varied parameter; and
select the fixed value of the parameter to use for subsequent irradiation of the sample based on the fitted curve.

12. The system of claim 11, wherein the image quality metric includes a focus index (FI) expressed as:

$$FI = \left[\sum_{i=0}^{n-1} \sqrt{(I*S_1 - I*S_2)^2}\right]/n,$$

where I represents an image of the sample, $S_1$ and $S_2$ represent 2D Gaussian functions of shorter and longer length scales, respectively, than a resolution limit of the scanning electron microscope system, i represents a pixel in the image, and n represents a total number of pixels considered in the image.

13. The system of claim 10, wherein different values of the parameter are selected for different tiles of an image of a surface of the sample.

14. The system of claim 10, wherein the parameter is a focus of the primary electron beam.

15. The system of claim 10, wherein the parameter is one of an astigmatism of the primary electron beam, or an aperture alignment of the primary electron beam.

* * * * *